United States Patent [19]

Failli et al.

[11] Patent Number: 5,120,726
[45] Date of Patent: Jun. 9, 1992

[54] RAPAMYCIN HYDRAZONES

[75] Inventors: Amedeo A. Failli, Princeton Junction; Robert J. Steffan, Langhorne, both of N.J.

[73] Assignee: American Home Products Corporation, New York, N.Y.

[21] Appl. No.: 667,684

[22] Filed: Mar. 8, 1991

[51] Int. Cl.⁵ .................. A61K 31/395; C07D 491/06
[52] U.S. Cl. .................. 514/183; 514/321; 540/456
[58] Field of Search .................. 540/456; 514/183, 321

[56] References Cited

U.S. PATENT DOCUMENTS

| | | | |
|---|---|---|---|
| 3,929,992 | 12/1975 | Seghal et al. | 424/122 |
| 3,993,749 | 11/1976 | Seghal et al. | 424/122 |
| 4,316,885 | 2/1982 | Rakhit | 424/122 |
| 4,401,653 | 8/1983 | Eng | 424/114 |
| 4,650,803 | 3/1987 | Stella et al. | 546/90 |
| 4,885,171 | 12/1989 | Surendra et al. | 424/122 |

OTHER PUBLICATIONS

J. Antibiot. 28,721-726 (1975).
J. Antibiot. 28,727-732 (1975).
J. Antibiot. 31,539-545 (1978).
Can. J. Physiol. Pharmacol. 55,48 (1977).
FASEB 3,3411 (1989).
FASEB 3,5256 (1989).
Lancet, pp. 1183-1185 (1978).
Med. Sci. Res., pp. 877-878 (1989), vol. 17.
J. Am. Chem. Soc., vol. 103, pp. 3215-3217 (1981).

*Primary Examiner*—Robert T. Bond
*Attorney, Agent, or Firm*—Arnold S. Milowsky

[57] ABSTRACT

A compound of the structure

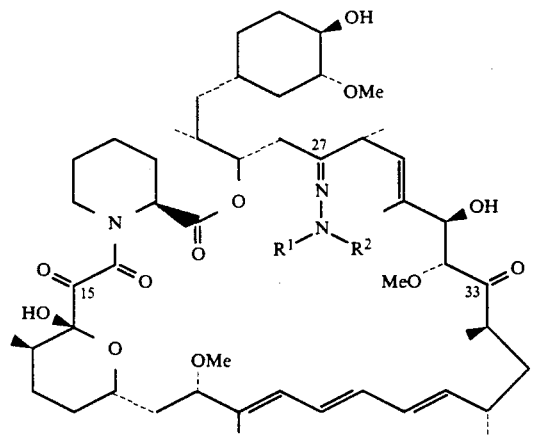

wherein
$R^1$ is hydrogen, alkyl or aralkyl; $R^2$ is hydrogen, alkyl, cycloalkyl, aralkyl, $-COR^3$, $-CO_2R^3$, $-SO_2R^3$, $-CONR^4R^5$, $-CSNR^4R^5$, $-COCONR^4R^5$, or Ar; $R^3$ is alkyl, aralkyl, or Ar; $R^4$ and $R^5$ are each, independently, hydrogen, alkyl, cycloalkyl, allyl, aralkyl, or Ar;
Ar is

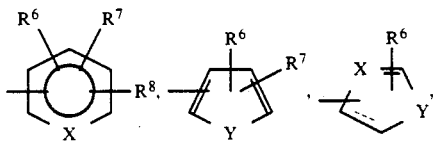

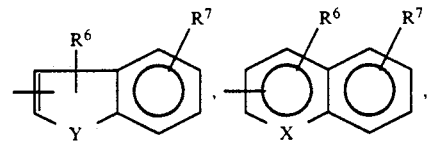

or

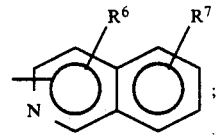

$R^6$, $R^7$, $R^8$ are each, independently, hydrogen, alkyl, alkoxy, hydroxy, cyano, halo, nitro, carbalkoxy, trifluoromethyl, trifluoromethoxy, amino, or a carboxylic acid; X is CH or N; Y is NH, O, or S; or a pharmaceutically acceptable salt thereof, which by virtue of its immunosuppressive activity is useful in treating transplantation rejection, host vs. graft disease, autoimmune diseases and diseases of inflammation; by virtue of its antitumor activity is useful in treating solid tumors; and by virtue of its antifungal activity is useful in treating fungal infections.

18 Claims, No Drawings

RAPAMYCIN HYDRAZONES

BACKGROUND OF THE INVENTION

This invention relates to hydrazones of rapamycin and a method for using them in the treatment of transplantation rejection, host vs. graft disease, autoimmune diseases, diseases of inflammation, solid tumors, and fungal infections.

Rapamycin is a macrocyclic triene antibiotic produced by *Streptomyces hygroscopicus*, which was found to have antifungal activity, particularly against *Candida albicans*, both in vitro and in vivo [C. Vezina et al., J. Antibiot. 28, 721 (1975); S. N. Sehgal et al., J. Antibiot. 28, 727 (1975); H. A. Baker et al., J. Antibiot. 31, 539 (1978); U.S. Pat. No. 3,929,992; and U.S. Pat. No. 3,993,749].

Rapamycin alone (U.S. Pat. No. 4,885,171) or in combination with picibanil (U.S. Pat. No. 4,401,653) has been shown to have antitumor activity. R. Martel et al. [Can. J. Physiol. Pharmacol. 55, 48 (1977)] disclosed that rapamycin is effective in the experimental allergic encephalomyelitis model, a model for multiple sclerosis; in the adjuvant arthritis model, a model for rheumatoid arthritis; and effectively inhibited the formation of IgE-like antibodies.

The immunosuppressive effects of rapamycin have been disclosed in FASEB 3, 3411 (1989) and its ability to prolong survival time of organ grafts in histoincompatible rodents was disclosed by R. Morris [Med. Sci. Res. 17: 877 (1989)]. The ability of rapamycin to inhibit T-cell activation was disclosed by M. Strauch [FASEB 3: 3411 (1989)]. Cyclosporin A and FK-506, other macrocyclic molecules, also have been shown to be effective as immunosuppressive agents, therefore useful in preventing transplant rejection [FASEB 3, 3411 (1989); FASEB 3, 5256 (1989); and R. Y. Calne et al., Lancet 1183 (1978)].

Mono- and diacylated derivatives of rapamycin (esterified at the 28 and 43 positions) have been shown to be useful as antifungal agents (U.S. Pat. No. 4,316,885) and used to make water soluble prodrugs of rapamycin (U.S. Pat. No. 4,650,803). Recently, the numbering convention for rapamycin has been changed; therefore according to Chemical Abstracts nomenclature, the esters described above would be at the 31- and 42-positions.

DESCRIPTION OF THE INVENTION

This invention provides derivatives of rapamycin which are useful as immunosuppressive, anti-inflammatory, and antifungal agents having the structure

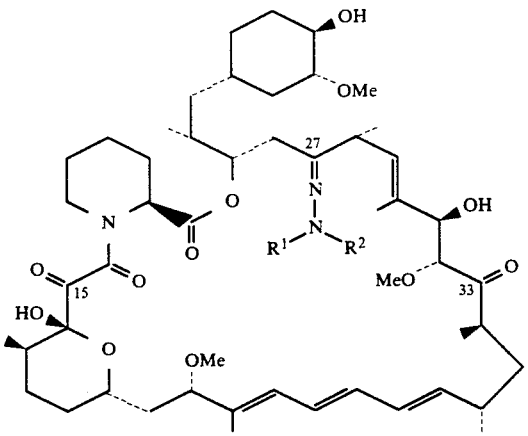

wherein
$R^1$ is hydrogen, alkyl of 1-6 carbon atoms, or aralkyl of 7-10 carbon atoms;
$R^2$ is hydrogen, alkyl of 1-6 carbon atoms, cycloalkyl of 3-10 carbon atoms, aralkyl of 7-10 carbon atoms, $-COR^3$, $-CO_2R^3$, $-SO_2R^3$, $-CONR^4R^5$, $-CSNR^4R^5$, $-COCONR^4R^5$, or Ar;
$R^3$ is alkyl of 1-6 carbon atoms, aralkyl of 7-10 carbon atoms, or Ar;
$R^4$ and $R^5$ are each, independently, hydrogen, alkyl of 1-6 carbon atoms, cycloalkyl of 3-10 carbon atoms, allyl, aralkyl of 7-10 carbon atoms, or Ar;
Ar is

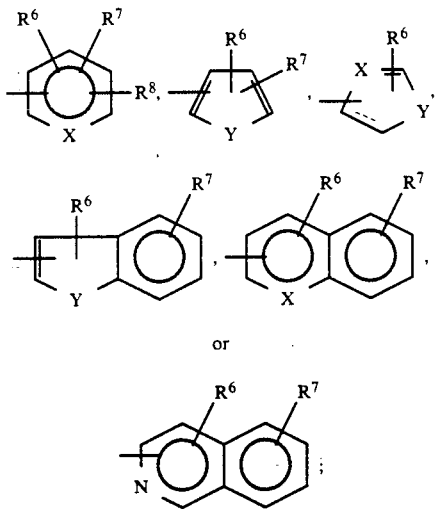

$R^6$, $R^7$, $R^8$ are each, independently, hydrogen, alkyl of 1-6 carbon atoms, alkoxy of 1-6 carbon atoms, hydroxy, cyano, halo, nitro, carbalkoxy of 2-7 carbon atoms, trifluoromethyl, trifluoromethoxy, amino, or a carboxylic acid;
X is CH or N;
Y is NH, O, or S;
or a pharmaceutically acceptable salt thereof.

The pharmaceutically acceptable salts are those derived from such organic and inorganic acids such as: acetic, lactic, citric, tartaric, succinic, maleic, malonic, gluconic, hydrochloric, hydrobromic, phosphoric, nitric, sulfuric, methanesulfonic, and similarly known acceptable acids.

Of these compounds, preferred members are those in which $R^1$ is hydrogen; those in which $R^2$ is —$CONR^4R^5$; those in which $R^1$ is hydrogen and $R^2$ is —$CONR^4R^5$; those in which $R^1$ is hydrogen, $R^2$ is —$CONR^4R^5$, and $R^5$ is Ar; those in which $R^2$ is —$COR^3$; those in which $R^1$ is hydrogen and $R^2$ is —$COR^3$; those in which $R^2$ is Ar; those in which $R^1$ is hydrogen, $R^2$ is Ar; those in which $R^1$ is hydrogen, $R^2$ is Ar, and

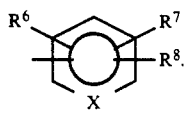

Although compounds of this invention can be prepared by conventional methods that are described in the literature, because functional groups are contained in a large macrocycle ring, functional groups reactivity cannot be readily predicted [R. B. Woodward et al., J. Am. Chem. Soc. 103, 3215, (1981)].

Rapamycin has carbonyl groups at 15, 27 and 33 positions. Based on X-ray crystallographic analysis the 33 function was predicted to be the most reactive center; unexpectedly however, hydrazone formation occurred predominantly at the 27 position.

The compounds of this invention can be prepared by the following route from rapamycin:

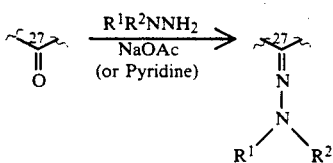

The hydrazine derivatives (hydrazines, semicarbazides, semithiocarbazides, and semioxamazides) used to prepare the compounds of the invention are commercially available or can be prepared by methods that are disclosed in the literature.

Immunosuppressive activity was evaluated in an in vitro standard pharmacological test procedure to measure lymphocyte proliferation (LAF) and in two in vivo standard pharmacological test procedures. The first in vivo procedure was a popliteal lymph node (PLN) test procedure which measured the effect of compounds of this invention on a mixed lymphocyte reaction and the second in vivo procedure evaluated the survival time of a pinch skin graft.

The comitogen-induced thymocyte proliferation procedure (LAF) was used as an in vitro measure of the immunosuppressive effects of representative compounds. Briefly, cells from the thymus of normal BALB/c mice are cultured for 72 hours with PHA and IL-1 and pulsed with tritiated thymidine during the last six hours. Cells are cultured with and without various concentrations of rapamycin, cyclosporin A, or test compound. Cells are harvested and incorporated radioactivity is determined. Inhibition of lymphoproliferation is assessed as percent change in counts per minute from non-drug treated controls. The results are expressed by the following ratio, or as the percent inhibition of lymphoproliferation at 1 μM.

$$\frac{^3\text{H-control thymus cells} - \text{H}^3\text{-rapamycin-treated thymus cells}}{^3\text{H-control thymus cells} - \text{H}^3\text{-test compound-treated cells}}$$

A mixed lymphocyte reaction (MLR) occurs when lymphoid cells from genetically distinct animals are combined in tissue culture. Each stimulates the other to undergo blast transformation which results in increased DNA synthesis that can be quantified by the incorporation of tritiated thymidine. Since stimulating a MLR is a function of disparity at Major Histocompatibility antigens, an in vivo popliteal lymph node (PLN) test procedure closely correlates to host vs. graft disease. Briefly, irradiated spleen cells from BALB/c donors are injected into the right hind foot pad of recipient C3H mice. The drug is given daily, p.o. from Day 0 to Day 4. On Day 3 and Day 4, tritiated thymidine is given i.p., b.i.d. On Day 5, the hind popliteal lymph nodes are removed and dissolved, and radioactivity counted. The corresponding left PLN serves as the control for the PLN from the injected hind foot. Percent suppression is calculated using the non-drug treated animals as allogenic control. Rapamycin at a dose of 6 mg/kg, p.o. gave 86% suppression, whereas cyclosporin A at the same dose gave 43% suppression. Results are expressed by the following ratio:

$$\frac{^3\text{H-PLN cells control C3H mouse} - \text{}^3\text{H-PLN cells rapamycin-treated C3H mouse}}{^3\text{H-PLN cells control C3H mouse} - \text{}^3\text{H-PLN cells test compound-treated C3H mouse}}$$

The second in vivo test procedure is designed to determine the survival time of pinch skin graft from male DBA/2 donors transplanted to male BALB/c recipients. The method is adapted from Billingham R. E. and Medawar P. B., J. Exp. Biol. 28:385–402, (1951). Briefly, a pinch skin graft from the donor is grafted on the dorsum of the recipient as a homograft, and an autograft is used as control in the same region. The recipients are treated with either varying concentrations of cyclosporin A as test control or the test compound, intraperitoneally. Untreated recipients serve as rejection control. The graft is monitored daily and observations are recorded until the graft becomes dry and forms a blackened scab. This is considered as the rejection day. The mean graft survival time (number of days±S.D.) of the drug treatment group is compared with the control group.

The following table summarizes the results of representative compounds of this invention in these three standard test procedures.

TABLE 1

| Compound | LAF (ratio)* | IC$_{50}$ (nM) | PLN (ratio)* | Skin Graft (days + SD) |
|---|---|---|---|---|
| Example 1 | 0.50 | 17.3 | + | 10.50 ± 0.6 |
| Example 2 | 0.45 | 19.2 | + | 7.83 ± 1.3 |
| Example 3 | 0.55 | 15.9 | + | + |
| Example 4 | 0.24 | 37.2 | 1.07 | + |
| Rapamycin | 1 | 8.5–8.8 | 1 | 12.0 ± 1.7 |

*Calculation of ratios was described supra.
+Not evaluated

The results of these standard pharmacological test procedures demonstrate immunosuppressive activity both in vitro and in vivo for the compounds of this invention. Positive ratios in the LAF and PLN test procedures indicate suppression of T cell proliferation. As a transplanted pinch skin grafts are typically rejected within 6-7 days without the use of an immunosuppressive agent, the increased survival time of the skin graft when treated with the compounds of this invention further demonstrates their utility as immunosuppressive agents.

Because the compounds of this invention are structurally similar to rapamycin and have a similar activity profile to rapamycin, the compounds of this invention also are considered to have antitumor and antifungal activities.

Based on the results of these standard pharmacological test procedures, the compounds are useful in the treatment of transplantation rejection such as, heart, kidney, liver, bone marrow, skin transplants and the like; autoimmune diseases such as, lupus, rheumatoid arthritis, diabetes mellitus, myasthenia gravis, multiple sclerosis and the like; and diseases of inflammation such as, psoriasis, dermatitis, eczema, seborrhea, inflammatory bowel disease uveitis, and the like; diseases of pulmonary inflammation, such as, asthma, chronic obstructive pulmonary disease, emphysema, acute respiratory distress syndrome, bronchitis, and the like; solid tumors; and fungal infections.

The compounds may be administered neat or with a pharmaceutical carrier to a mammal in need thereof. The pharmaceutical carrier may be solid or liquid.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, methyl cellulose, sodium carboxymethyl cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by, for example, intramuscular, intraperitoneal or subcutaneous injection. Sterile solutions can also be administered intravenously. The compounds can be administered orally either in liquid or solid composition form. The compounds also may be administered rectally in the form of a conventional suppository. For administration by intranasal or intrabronchial inhalation, or insufflation, the compounds may be formulated into an aqueous or partially aqueous solution, which can be utilized in the form of an aerosal.

The dosage requirements vary with the particular compositions employed, the route of administration, the severity of the symptoms presented and the particular subject being treated. Treatment will generally be initiated with small dosages less than the optimum dose of the compound. Thereafter the dosage is increased until the optimum effect under the circumstances is reached; precise dosages for oral, parenteral, intranasal, intrabronchial, or rectal administration will be determined by the administering physician based on experience with the individual subject treated.

Preferably, the pharmaceutical composition is in unit dosage form, e.g. as tablets or capsules. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. The dosage to be used in the treatment must be subjectively determined by the attending physician.

In addition, the compounds of this invention may be employed as a solution, cream, or lotion by formulation with pharmaceutically acceptable vehicles containing 0.1-0.5 percent, preferably 2%, of active compound which may be administered to a fungally affected area.

The following examples illustrate the preparation of representative compounds of this invention.

EXAMPLE 1

Rapamycin 27-(methylcarbonyl hydrazone)

Under anhydrous conditions, a mixture of rapamycin (2.5 g, 2.7 mmole) and acethydrazide (0.3 g, 4.1 mmole) in 2.5 mL of pyridine were heated at 60° C. overnight. The reaction mixture was concentrated under reduced pressure and the residue triturated with water. The precipitate was collected, washed with water and dried in vacuo to yield 0.62 g of crude product which was further purified by flash chromatography (on silica gel Merck 60, eluant ethyl acetate).

$^1$H NMR (CDCl$_3$, 400 MHz): δ 1.599 (s, 3H, CH$_3$C=C), 1.652 (s, 3H, CH$_3$C=C),2.253 (s, 3H, CH$_3$CO), 3.163 (s, 3H, CH$_3$O), 3.314 (s, 3H, CH$_3$O), 3.40 (s, 3H, CH$_3$O), 8.482 (s, 1H, NNH—).

MS (neg. ion FAB, m/z): 969 (M−), 590,377

Anal. Calc'd for C$_{53}$H$_{83}$N$_3$O$_{13}$: C, 65.61; H, 8.62; N, 4.33. Found: C, 65.45; H, 8.42; N, 4.18.

The following representative compounds can be prepared from rapamycin and the appropriate hydrazine by employing the method used to prepare the title compound in Example 1.

Rapamycin 27-[(N-methyl N-methylcarbonyl)hydrazone]

Rapamycin 27-[(2-naphthylcarbonyl)hydrazone]
Rapamycin 27-[(4-chlorophenylcarbonyl)hydrazine]
Rapamycin 27-[(N-ethyl N-(4-hydroxyphenylcarbonyl))hydrazone]
Rapamycin 27-[(N-butyl N-(2-pyridylcarbonyl))hydrazone]
Rapamycin 27-[(2-furylcarbonyl)hydrazone]
Rapamycin 27-[(N-methylphenyl N-(2-(1-methylimidazolylcarbonyl)))hydrazone]
Rapamycin 27-[methoxycarbonyl hydrazone]
Rapamycin 27-[(N-(2-oxazolyl) N-((phenylmethoxy)carbonyl))hydrazone]
Rapamycin 27-[phenylsulfonyl hydrazone]
Rapamycin 27-[(N-(4-chlorophenyl) N-(4-methylphenylsulfonyl))hydrazone]

EXAMPLE 2

Rapamycin 27-(4-Phenylsemicarbazone)

A solution of rapamycin (2 g, 2.2 mmole), phenylsemicarbazide (0.33 g, 2.2 mmole) and sodium acetate (0.18 g, 2.2 mmole) in dry methanol (10 mL) was heated at 60° C. for 6 hrs. After stirring overnight at room temperature, the reaction mixture was diluted with 50 mL of water. The precipitate was collected, washed with water and dried to yield 2.3 g of crude product. Purification was achieved by MPLC (on Lobar silica gel Merck 60, ethyl acetate-methanol 98:2, flow rate 20 mL/min).

$^1$H NMR (CDCl$_3$, 400 MHz): δ 1.646 (s, 3H, CH$_3$C=C), 1.805 (s, 3H, CH$_3$C=C), 3.150 (s, 3H, CH$_3$O), 3.312 (s, 3H, CH$_3$O), 3.402 (s, 3H, CH$_3$O), 7.049 (t, 1H, ArH), 7.297 (t, 2H, ArH), 7.49 (d, 2H, ArH), 8.17 (s, 1H, NH), 8.29 (broad, 1H, NH).

$^{13}$C NMR (CDCl$_3$, 400 MHz): 212.7, 191.87, 168.95, 167.01, 153.56, 150.93, 138.69, 98.48

MS (neg.ion FAB, m/z): 1045 (M-H$^-$), 590,454

Anal. Calcd. for C$_{58}$H$_{86}$N$_4$O$_{13}$.H$_2$O; C, 65.39; H, 8.32; N, 5.26. Found: C, 65.00; H, 8.22; N, 5.29.

The following representative compounds can be prepared from rapamycin and the appropriate semicarbazide, semithiocarbazide, or semioxamazide by employing the method used the prepare the title compound in Example 2.

Rapamycin 27-(4-methyl 4-phenylsemicarbazone)
Rapamycin 27-(4-(2-pyridyl) 4-methylsemicarbazone)
Rapamycin 27-(4-(3-isoquinolinyl)semicarbazone)
Rapamycin 27-(4-phenylsemithiocarbazone)
Rapamycin 27-(4,4-diphenylmethylsemithiocarbazone)
Rapamycin 27-(5-phenylsemioxamazone)
Rapamycin 27-(5-(phenylmethyl) 5-propylsemioxamazone)

EXAMPLE 3

Rapamycin 27-(2-Pyridinylhydrazone)

Under anhydrous conditions, a solution of rapamycin (1 g, 1.1 mmole), 2-hydrazino pyridine dihydrochloride (0.3 g, 1.65 mmole) and anhydrous sodium acetate (0.4 g, 4.95 mmole) in 10 mL of anhydrous methanol was heated at reflux for 1 hour. The reaction mixture was diluted with water and the precipitate is collected, washed with water and dried in vacuo. Purification of the crude product by flash chromatography (on silica gel Merck 60, gradient from 19:1 dichloromethane-ethyl acetate gradient to pure ethyl acetate) provides the pure title compound most likely as a mixture of E and Z isomers (based upon the NMR spectral data).

$^1$H NMR (CDCl$_3$, 400 MHz): δ 1.639 and 1.691 (2s, 3H, CH$_3$C=C), 1.788 (s, 3H, CH$_3$C=C), 3.135 and 3.152 (2s, 3H, CH$_3$O), 3.27, 3.274 and 3.296 (3s, 3H, CH$_3$O), 3.413 (s, 3H, CH$_3$O), 6.68-6.74 (m, 1H, ArH), 7.19-7.24 (m, 1H, ArH), 7.51-7.58 (m, 1H, ArH), 7.99 (s, 1H, NH), 8.03-8.08 (m, 1H, ArH).

MS (neg. ion FAB, m/z): 1004 (M$^-$), 590,412

Anal, Calcd. for C$_{56}$H$_{84}$N$_4$O$_{12}$.0.4H$_2$O: C, 66.43; H, 8.44; N, 5.53. Found: C, 66.19; H, 8.08; N, 5.82.

The following representative compounds can be prepared from rapamycin and the appropriate hydrazine by employing the method used to prepare the title compound in Example 3.

Rapamycin 27-(phenylhydrazone)
Rapamycin 27-(N-methyl N-(4(1,4-tetrahydrooxazinyl))hydrazone)
Rapamycin 27-(N-phenylmethyl N-(4-thiazolyl)hydrazone)
Rapamycin 27-(N-(3,4-dihydroxyphenyl) N-cyclohexylhydrazone
Rapamycin 27-(N-methyl N-(2-indolylhydrazone)
Rapamycin 27-(2-thionaphthylhydrazone)
Rapamycin 27-(N,N-dimethylhydrazone)

EXAMPLE 4

Rapamycin 27-semicarbazone

A solution of rapamycin (1.5 g, 1.6 mmole), semicarbazide hydrochloride (0.29 g, 2.45 mmole) and anhydrous sodium acetate (0.39 g, 4,8 mmole) in anhydrous methanol(15 mL) was heated at 50° C. for 14 hours. The mixture was diluted with water, the precipitate is collected, washed with water and dried in vacuo. The crude product was purified by MPLC (on Lichrosorb RP-8, 310-25 Merck, acetonitrile-water 55:45, flow rate 20 mL/min) to provide the pure title compound.

$^1$H NMR (CDCl$_3$, 400 MHz): δ 1.654 (s,3H, CH$_3$C=C), 1.784 (s, 3H, CH$_3$C=C), 3.133 and 3.169 (2s, 3H, CH$_3$O), 3.305 (s,3H, CH$_3$O), 3.412, 3.414 and 3.426 (3s, 3H, CH$_3$O), 7.93 (broad, 1H, NH), 8.47 (broad, 2H, NH2)

$^{13}$C NMR (CDCl$_3$, 400 MHz): 216.35, 191.19, 170.38, 168.56, 167.11, 167.02, 157.73, 157.32, 98.97, 98.34, 98.25

MS (neg ion FAB, m/z): 970 (M$^-$), 590

Anal. Calcd for C$_{52}$H$_{82}$N$_4$O$_{13}$.0.75H$_2$O: C, 63.62; H, 8.55; N, 5.60. Found: C, 63.58; H, 8.47; N, 5.79.

The following representative compounds can be prepared from rapamycin semithiocarbazide and semithiocarbazide by employing the method used tp prepare the title compound in Example 4.

Rapamycin 27-semithiocarbazone
Rapamycin 27-semioxamazone

EXAMPLE 5

Rapamycin 27-hydrazone

A solution of Rapamycin (0.1 g, 0.11 mmole) and 85% hydrazine hydrate (0.0065 g, 0.11 mmole) in anhydrous methanol (1 mL) was heated in an oil bath at 60° C. overnight. The mixture was concentrated in vacuo and the residue was purified by preparative TLC (on 20×20 cm Merck-60 silica gel plates, eluant: dichloromethanemethanol 9:1) to provide the pure title compound as a white solid.

$^1$H NMR (CDCl$_3$, 400 MHz): δ 1.71 (m, 3H, CH$_3$C=C), 1.728 (m, 3H, CH$_3$C=C), 3.14 (s, 3H, CH$_3$O), 3.415 (s, 6H, CH$_3$O), 6.786 (broad, 2H, NH2).

MS (neg ion FAB, m/z): 927 (M)$^-$

What is claimed is:

1. A compound of the formula wherein
R[1] is hydrogen, alkyl of 1-6 carbon atoms, or phenylalkyl of 7-10 carbon atoms;
R[2] is hydrogen, alkyl of 1-6 carbon atoms, cycloalkyl of 3-10 carbon atoms, phenylalkyl 7-10 carbon atoms, —COR[3], —CO$_2$R[3], —SO$_2$R[3], —CONR[4]R[5], —CSNR[4]R[5], —COCONR[4]R[5], or Ar;
R[3] is alkyl of 1-6 carbon atoms, phenylalkyl of 7-10 carbon atoms, or Ar;
R[4] and R[5] are each, independently, hydrogen, alkyl of 1-6 carbon atoms, cycloalkyl of 3-10 carbon atoms, allyl, phenylalkyl of 7-10 carbon atoms, or Ar;
Ar is R[6], R[7], R[8] are each, independently, hydrogen, alkyl of 1-6 carbon atoms, alkoxy of 1-6 carbon atoms, hydroxy, cyano, halo, nitro, carbalkoxy of 2-7 carbon atoms, trifluoromethyl, trifluoromethoxy, amino, or —CO$_2$H;
X is CH or N;
Y is NH, O, or S;
or a pharmaceutically acceptable salt thereof.

2. A compound of claim 1 where R[1] is hydrogen or a pharmaceutically acceptable salt thereof.

3. A compound of claim 1 where R[2] is —CONR[4]R[5] or a pharmaceutically acceptable salt thereof.

4. A compound of claim 1 where R[1] is hydrogen and R[2] is —CONR[4]R[5] or a pharmaceutically acceptable salt thereof.

5. A compound of claim 1 where R[1] is hydrogen, R[2] is —CONR[4]R[5], and R[5] is Ar or a pharmaceutically acceptable salt thereof.

6. A compound of claim 1 where R[2] is —COR[3] or a pharmaceutically acceptable salt thereof.

7. A compound of claim 1 where R[1] is hydrogen and R[2] is —COR[3] or a pharmaceutically acceptable salt thereof.

8. A compound of claim 1 where R[2] is Ar or a pharmaceutically acceptable salt thereof.

9. A compound of claim 1 where R[1] is hydrogen and R[2] is Ar or a pharmaceutically acceptable salt thereof.

10. A compound of claim 1 where R[1] is hydrogen, R[2] is Ar, and Ar is or a pharmaceutically acceptable salt thereof.

11. A compound of claim 1 which is rapamycin 27-(methylcarbonylhydrazone) or a pharmaceutically acceptable salt thereof.

12. A compound of claim 1 which is rapamycin 27-(4-phenylsemicarbazone) or a pharmaceutically acceptable salt thereof.

13. A compound of claim 1 which is rapamycin 27-(2-pyridinylhydrazone), or a pharmaceutically acceptable salt thereof.

14. A compound of claim 1 which is rapamycin 27-semicarbazone or a pharmaceutically acceptable salt thereof.

15. A compound of claim 1 which is rapamycin 27-hydrazone or a pharmaceutically acceptable salt thereof.

16. A method of treating transplantation rejection, host vs. graft disease, autoimmune diseases, and diseases of inflammation in a mammal by administering an effective amount of a compound having the formula wherein
R[1] is hydrogen, alkyl of 1-6 carbon atoms, or phenylalkyl of 7-10 carbon atoms;

$R^2$ is hydrogen, alkyl of 1-6 carbon atoms, cycloalkyl of 3-10 carbon atoms, phenylalkyl of 7-10 carbon atoms, —$COR^3$, —$CO_2R^3$, —$SO_2R^3$, —$CONR^4R^5$, —$CSNR^4R^5$, —$COCONR^4R^5$, or Ar;

$R^3$ is alkyl of 1-6 carbon atoms, phenylalkyl of 7-10 carbon atoms, or Ar;

$R^4$ and $R^5$ are each, independently, hydrogen, alkyl of 1-6 carbon atoms, cycloalkyl of 3-10 carbon atoms, allyl, phenylalkyl of 7-10 carbon atoms, or Ar;

Ar is

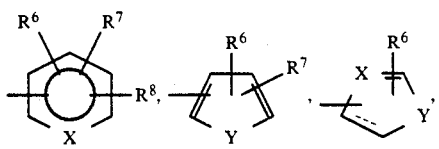

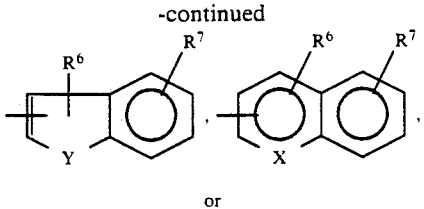

or

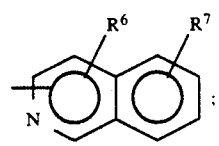

$R^6$, $R^7$, $R^8$ are each, independently, hydrogen, alkyl of 1-6 carbon atoms, alkoxy of 1-6 carbon atoms, hydroxy, cyano, halo, nitro, carbalkoxy of 2-7 carbon atoms, trifluoromethyl, trifluoromethoxy, amino, or —$CO_2H$;

X is CH or N;

Y is NH, O, or S;

or a pharmaceutically acceptable salt thereof.

17. A pharmaceutical composition for use as an immunosuppressive agent comprising an immunosuppressive amount of a compound of claim 1.

18. A composition as claimed in claim 17 in unit dosage form.

* * * * *